United States Patent [19]

Inglese

[11] Patent Number: 5,363,135
[45] Date of Patent: Nov. 8, 1994

[54] ENDOSCOPE HAVING A SEMI-CONDUCTOR ELEMENT ILLUMINATION ARRANGEMENT

[76] Inventor: Jean-Marc Inglese, 4 Impasse des Chênes, 78112 Fourqueux, France

[21] Appl. No.: 49,507

[22] Filed: Apr. 19, 1993

[30] Foreign Application Priority Data

Apr. 21, 1992 [FR] France ................................ 92 04826

[51] Int. Cl.⁵ .............................................. A61B 1/06
[52] U.S. Cl. ......................................... 348/70; 348/66; 348/223; 433/29
[58] Field of Search ...................... 358/42, 98; 433/29; 348/66, 70, 68, 223

[56] References Cited

U.S. PATENT DOCUMENTS

| | | | |
|---|---|---|---|
| 4,633,304 | 12/1986 | Nagasaki | 358/98 |
| 4,638,353 | 1/1987 | Nagasaki et al. | 358/98 |
| 4,884,133 | 11/1989 | Kanno et al. | 358/98 |
| 5,007,407 | 4/1991 | Kikuchi | 358/98 X |
| 5,027,138 | 6/1991 | Ganrud | 358/98 X |
| 5,049,070 | 9/1991 | Ademovic | 358/98 X |
| 5,178,536 | 1/1993 | Werly et al. | 433/29 |
| 5,187,572 | 2/1993 | Nakamura et al. | 358/98 |

FOREIGN PATENT DOCUMENTS

| | | |
|---|---|---|
| 0280823 | 9/1988 | European Pat. Off. . |
| 3411366 | 10/1985 | Germany . |
| 3718603 | 12/1987 | Germany . |
| 8911252 | 11/1989 | WIPO . |

*Primary Examiner*—Mark R. Powell
*Attorney, Agent, or Firm*—Steinberg, Raskin & Davidson

[57] ABSTRACT

A device for the acquisition of images of an object, of the type including a light emitting source for illuminating said object and a light sensor of the monochromic charge coupled device type and adapted to receive the light representative of the image of said object. The light source has at least one semi-conductor light emitter such as an electroluminescent or laser diode, the invention being usable for medical diagnosis purposes.

12 Claims, 3 Drawing Sheets

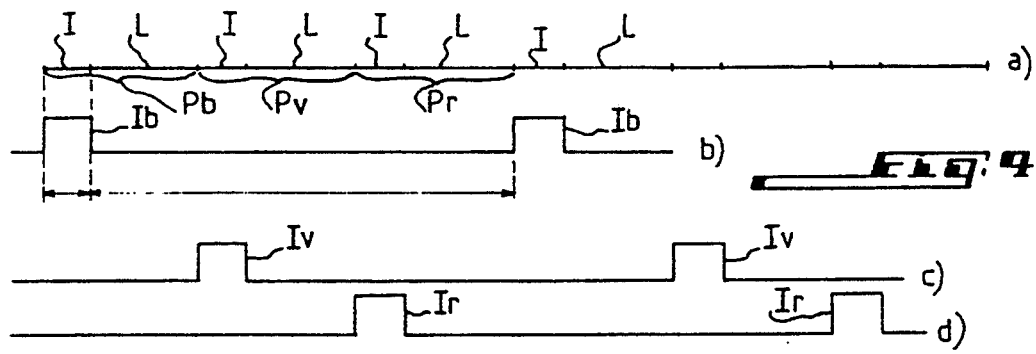
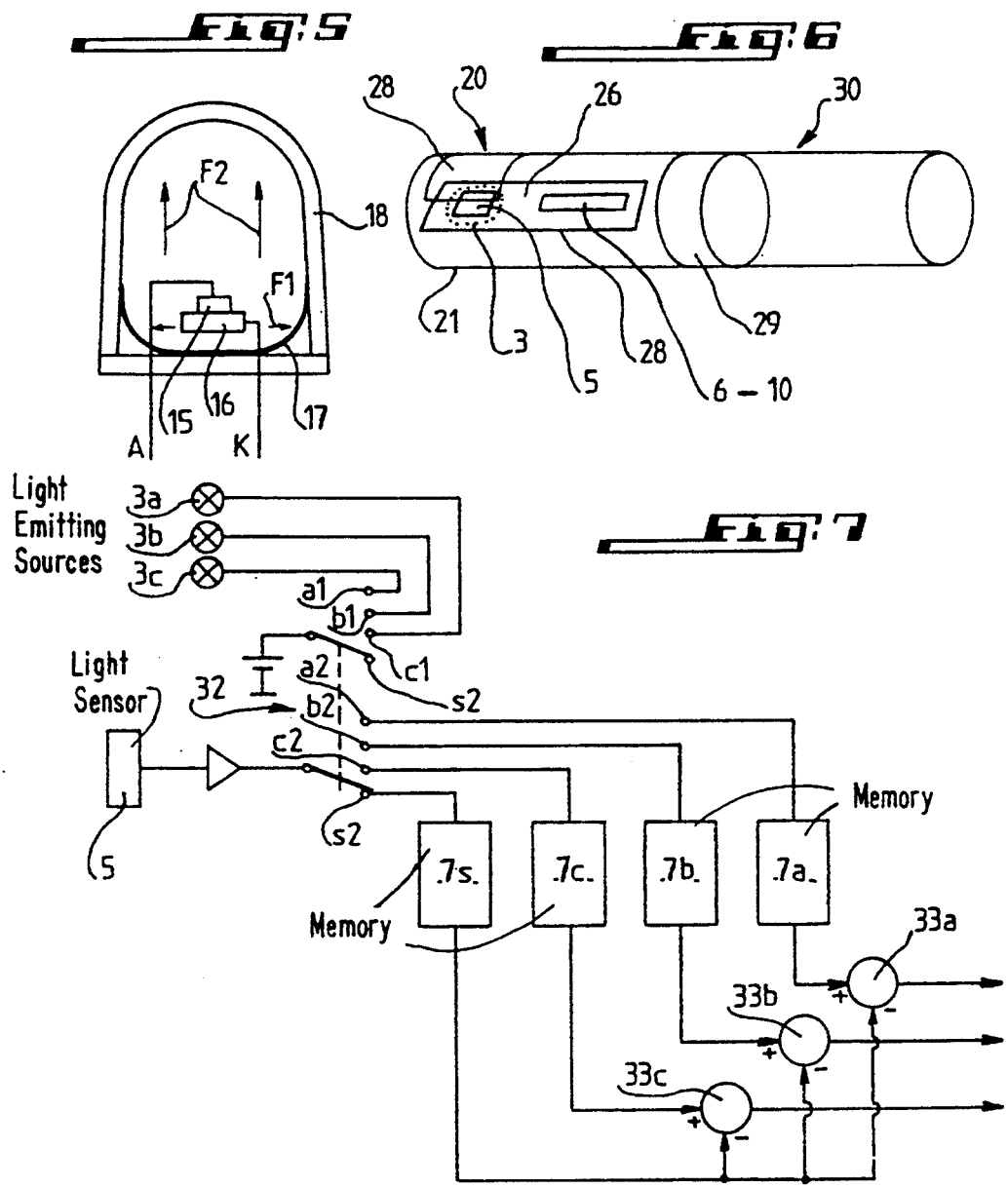

ENDOSCOPE HAVING A SEMI-CONDUCTOR ELEMENT ILLUMINATION ARRANGEMENT

FIELD OF THE INVENTION

The present invention relates to an image acquisition device.

Such a device comprises at least one source of illumination, a light sensor or gage and a system for the processing of signals originating from the sensor or gage.

BACKGROUND OF THE INVENTION

Now while it is indisputable that more and more the image acquisition devices are calling for sensors or gages the sizes and the weights of which are decreasing it is on the contrary in particular with the medical imagery systems relatively difficult to make use of illumination sources of small bulk and especially of low electrical power consumption.

The prior art made use of light sensors or gages which could either be monochromic or with colours. In the case of monochromatic sensors and with a purpose of taking coloured images, there has been carried out a trichromatic analysis from the primary colours obtained through mechanical switching of coloured filters in front of a white light source. In the case of colour sensors the white light was directly used. Now in the first case the mechanical switches exhibited inconveniences due to their consumptions, their bulks and their response times and in the second case the colour sensors offered lesser image definition and sensitivity.

OBJECT AND SUMMARY OF THE INVENTION

Therefore the object of the present invention is to provide a monochromous or coloured image acquisition device making use of a particularly simple technique of illumination with a low electrical power consumption associated with a monochromatic light sensor or gage having a great light sensitivity and a high definition.

More specifically the subject of the present invention is a colour image acquisition device characterized in that it comprises:

a monochromatic light sensor, an illumination source with a low electrical power consumption and with a short response time, electronic means for the control of the elements referred to hereinabove, electronic means adapted to store the signals delivered by the monochromatic light sensor and to reconstruct therefrom second signals consistent with the standards of operation of colour display or visualization screens, optional control means intended to be operated by the user.

The device according to the invention is moreover characterized in that the whole or one part of these elements may be integrated into one single optionally fluid-tight unit of small size.

BRIEF DESCRIPTION OF THE DRAWINGS

The invention will be better understood and further objects, characterizing features, details and advantages thereof will appear more clearly as the following explanatory description proceeds with reference to the accompanying diagrammatic drawings given by way of nonlimiting examples only and illustrating several presently preferred specific embodiments of the invention and in which:

FIG. 4 shows a graphic chart illustrating the different operating phases of a light sensor according to the invention and at a, b and c, the emission chronograms of the blue, green and red colour lights, respectively;

FIG. 5 is a diagrammatic view of a light source of an electroluminescent diode of the LED type;

FIG. 6 is a diagrammatic view of a second embodiment of an image acquisition device according to FIG. 1;

FIG. 7 illustrates as a block diagram an examplary embodiment of the device for the processing of the images originating from the light sensor according to the invention.

DETAILED DESCRIPTION OF THE INVENTION

Figure 1:
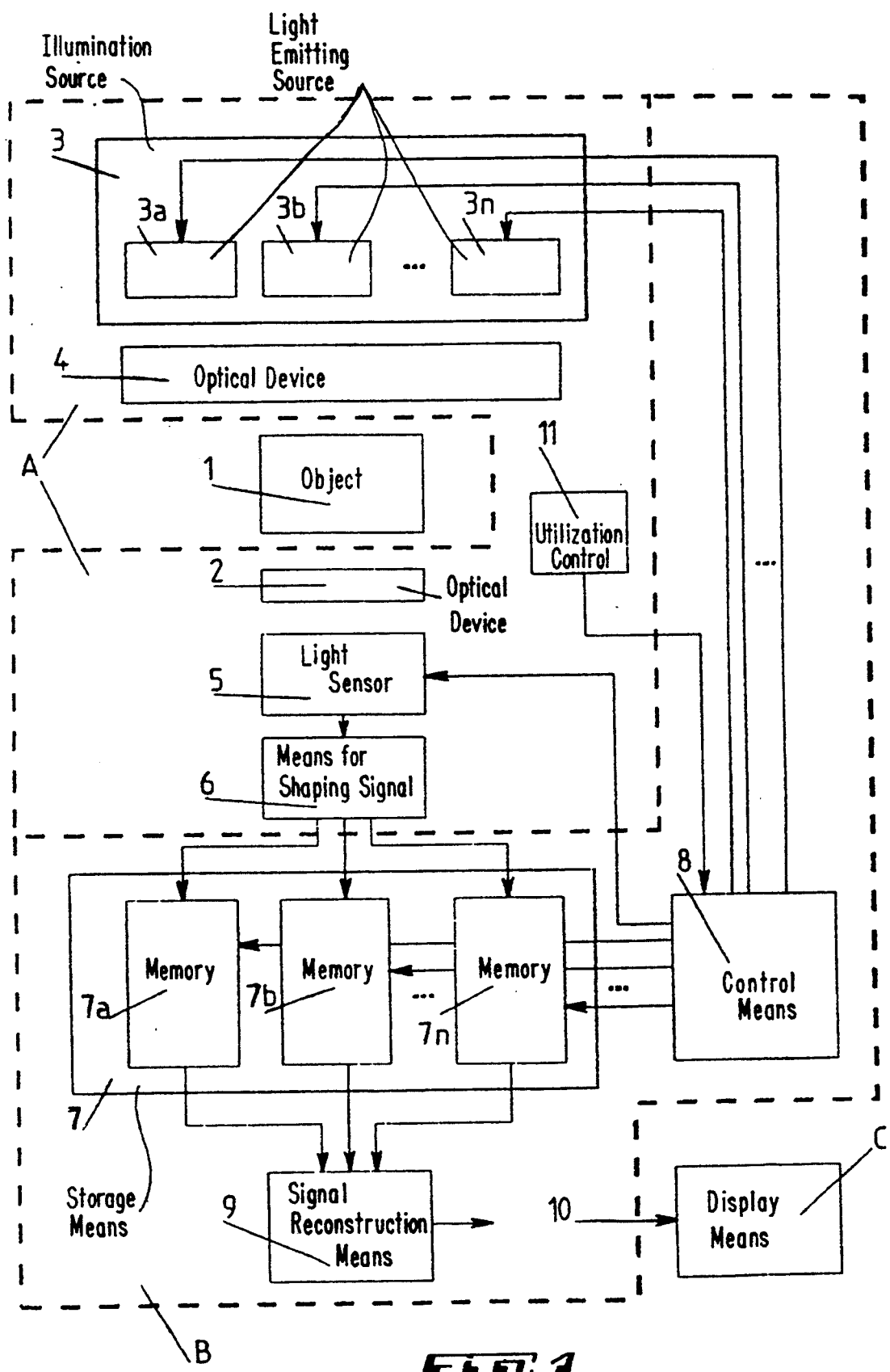
FIG. 1 shows as a block diagram an image acquisition device according to the present invention.

According to FIG. 1 a device according to the invention consists of two sub-assemblies (A) and (B) corresponding to the image acquisition and to the signal processing functions, respectively. The subassembly (A) comprises the illumination source (3), the optical devices (2) and (4), the light sensor (5) and optionally the utilization controls (11). The sub-assembly (B) comprises the electronic control means (8) and the electronic storage means (7) and standard signal reconstruction means (9). The sub-assembly (A) could for instance be integrated into one single hand-operated unit whereas the sub-assembly (B) could for instance be placed at a distance away or remote from the subject (1).

The image of the subject (1) is sent back through the optical device (2) towards the light sensor (5). The optical device (2) could consist for instance or an objective with lenses associated with mirrors or in the case for instance of an endoscopic application, of an image transfer device for instance of the kind with optical fibers.

The light sensor (5) should be of the so-called monochromatic C.C.D. or Charge Coupled Device type. The selection of the C.C.D. technology proceeds from the great light sensitivity of these sensors. The choice of a monochromic sensor is based upon two considerations which are the optical resolution at equal size and a better light sensitivity than those of the colour sensors. A C.C.D. colour sensor indeed is like a monochromic sensor except that in front of each sensitive element has been placed a tiny coloured filter. These filters are selected among the colours allowing the reconstruction of a coloured image with a natural appearence and associated by three (red, green, blue filters) or by four (yellow, green, magenta, cyan filters). A monochronic sensor therefore has in view of the absence of filters, a better light sensitivity due to the absence of absorption by the filter and a better optical resolution owing to the fact that all the sensitive elements are simultaneously used for one given colour.

Of course if it is desired to reconstruct a coloured image a colour analysis should be performed. It would be carried out for each one of the primary colours retained for the illumination source on the basis of one colour at a time.

Figure 3A:
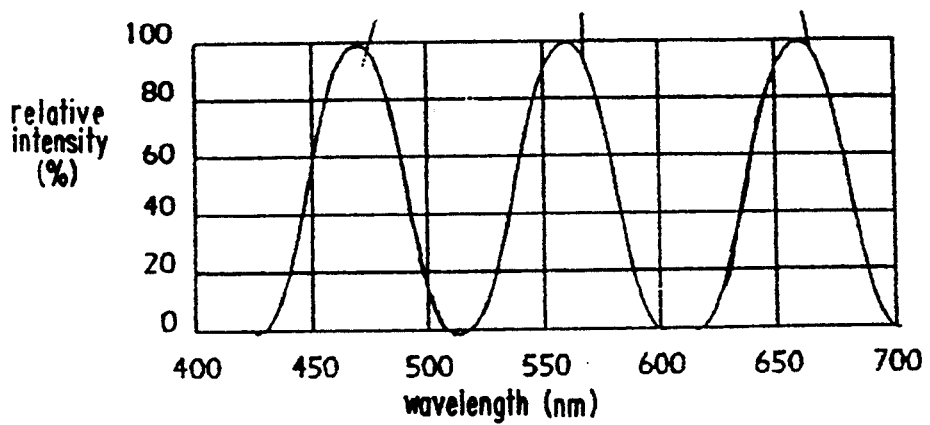
FIGS. 3a and 3b show two light spectra emitted by an illumination source according to the present invention.
Figure 3B:
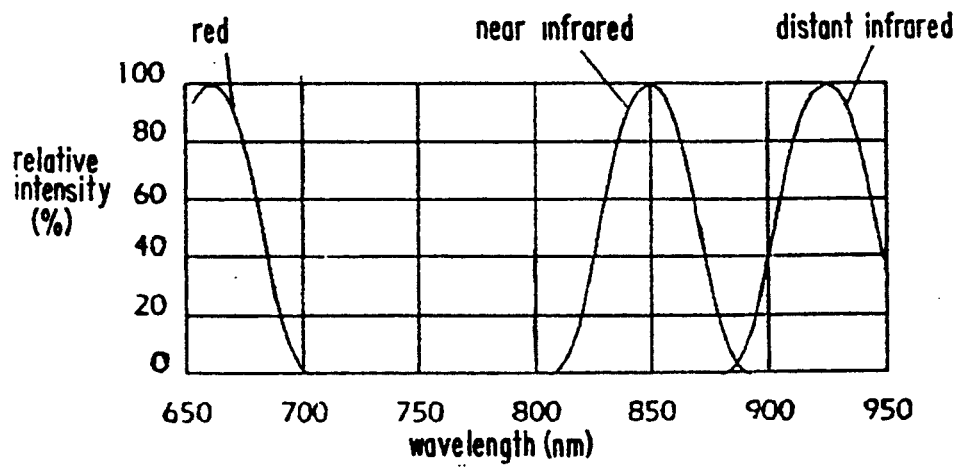

The illumination source (3) should consist of a number of primary light sources so as to reconstruct a natural appearance of the coloured images. Two examples of reconstruction of the natural light are provided by FIG. 3. The first example illustrated by FIG. 3a relates to visible colour image acquisitions. It makes use of a three-colour spectrum consisting of the primary red, green and blue colours. The second example illustrated by FIG. 3b relates to the image acquisition in the infrared range. It makes use of a three-colour spectrum consisting of the red, near infrared and distant infared primary colours.

The primary light sources should be selected so as to exhibit an emission spectrum which should be as pure and as close to the ideal primary colours as possible. Furthermore these sources should exhibit a very short response time since the analysis of the colours will be carried out sequentially. At last they should exhibit light emission levels consistent with the sensitivity of the light sensor used.

One should advantageously choose light sources calling for light emitters of the semi-conductor type, for example electroluminescent diodes (also known under the name of LED or Light Emitting Diodes) or for instance LASER diodes in the case of the infrared for instance.

In addition to the advantages referred to hereinabove the semi-conductor emitters are interesting because they accept overmodulation rates in the case of utilization of the impulse type, which will be the case owing to the sequential analysis of the colours thereby resulting in advantageous light emission powers.

Another basic characterizing feature of the light sources with semi-conductors is that during the operation in visible light, they do not emit unlike the other so-called "hot" light sources such for example as halogen bulbs, an undesirable amount of infrared radiation unless of course they are specifically selected for that purpose in the scope of a determined application. For that purpose the charged coupled device sensors are often provided with a filter which does not let the infrared radiation pass therethrough. In the present case this filter could therefore be omitted thereby resulting in a considerable increase of the sensitivity to light of the light sensor (5).

The invention permits to take into account emission powers of the electroluminescent diodes of the LED type which could be different from one colour to another one and for instance decrease from red to blue with a same diode activation current and also exhibit differences in sensitivity to the colours of the sensor 5.

To compensate for these differences it would be possible to therefore increase the activation current of the diodes or their number. In the first case in view of the small cyclic ratio of the light signals emitted by each diode and thus of the impulse operation mode thereof, the activation current could be increased without being afraid of an impairment of the diodes. Even strong overmodulations thus are possible.

FIG. 4 illustrates the small cyclic light emission ratio of the diodes. At a this FIGURE shows for each blue colour b, green colour v and red colour r both phases of the sensor (5), namely the phase of acquisition through integration I and the phase of reading L. Since for instance the blue diode only emits for a short time interval of integration I of the blue period Pb and is out of service or switched out for the periods of green light Pv and red light Pr, the cyclic ratio may have a very small value of 15% for example.

The relative light intensities of the primary light sources could of course be adjusted to take into account the non-linearity of the spectral response diagram of the light sensor (5).

FIG. 1 gives an example of association of a number n of primary sources $(3a), (3b), \ldots, (3n)$. Each primary source will consist of one or several semi-conductor emitters of the same emission spectrum.

It will be possible to optionally associate with these primary sources an optical device (4) in order to adjust their radiation space diagram. This optical device (4) could consist for instance of an objective with lenses associated with mirrors or in the case for example of an endoscopic application, of an image transfer device of the type with optical fibers for example.

FIG. 5 diagrammatically shows a light emitting device with a LED diode. On this FIGURE the reference numeral 15 designates the chip or semi-conductor element made for example from silicon, which is connected to the anode terminal A, the reference numeral 16 designates the substrate forming the cathode K upon which is laid the silicon chip 15 and the reference numeral 17 designates a reflector for orienting the produced light shown by arrows F I as a bundle F2 which will be emitted through the optical arrangement shown at 18 and forming part of the casing of the device.

Instead of placing one single semi-conductor element 15 upon the substrate 16, one could lay several elements thereon, distributed so as to give a uniform illumination of the object the image of which has to be taken and reproduced.

The switching on of each one of the primary sources should be operated by electronic control means (8). At the same time as the lighting of one of the three primary sources, the light sensor (5) should be put in the integration mode, i.e. it should perform the conversion of the light energy received as an electric charge within each one of its sensitive elements. The electronic control means (8) would then operate to extinguish or switch out the primary light source and the change of the light sensor (5) to the reading mode during which the electric charges, accumulated during the integration, will be available as output signals which could be shaped by electronic means for shaping electrical signals (6).

The shaped signals will be received into one of the pages of the electronic storage means (7) which will each one be capable of retaining at least once the whole screen of the light sensor (5). These electronic storage means should of course be organized so as to offer as many pages $(7a), (7b), \ldots, (7n)$ as they are primary colours retained.

The electronic control means (8) would then carry out the same sequence of operations for the following primary light source and so on.

When all the primary light sources will have been sequentially activated, the whole of the storage means (7) will contain the screens corresponding to the image of the object (1) illuminated by all the primary colours on the basis of one colour per page. During the restart of the cycle described hereinabove, the storage means could with the assistance of a multiplexing device they will be provided with, restore in parallel relationship the screens of the foregoing cycle and provide them as signals to the electronic means (9) which will convert these signals into second signals (10) consistent with the visualization standards.

Of course in order that this conversion be possible, it will be necessary that the cycles of acquisition of primary colour images be quicker than the cycle of the transfer of one colour image to the means of said second signals. The ratio between the duration of the acquisition cycle of one screen for one primary colour and the duration of the cycle of image transmission by means of standard visualization signals should be equal to the number of primary colours used by the illumination source.

These signals should advantageously be displayed by means (C) consisting for instance of television screens or of devices for the permanent storage of images. These means are known per se and will not be described.

Of course owing to the fact that all the screens corresponding to the image of the subject (1) will at any time be preserved or retained by the electronic storage means (7), the user will be able to suspend the cycle of taking images through a control means (11) which could consist for instance of a bottom located for instance onto the unit including the light sensor. The electronic control means will then suspend the acquisition cycle of screens while keeping activated the conversion function of the electronic means (9). One therefore will get an image freezing effect.

All of the means and devices referred to hereinabove and calling the technologies with high integration densities and low electrical power consumption, the image acquisition device using a light source with semi-conductors which is the subject matter of the present description could advantageously be integrated as a whole or in part into one single optionally fluid-tight and sterilizable unit of small size which could for instance put with portable visualizing or display devices fed by a self-contained energy source.

Figure 2:
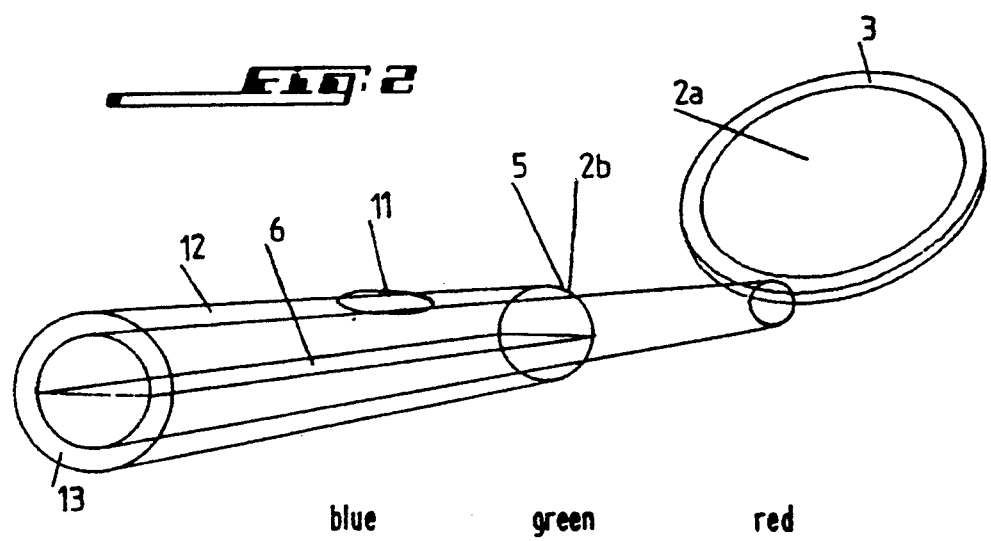
FIG. 2 shows a first examplary embodiment of the image acquisition device according to FIG. 1.

An exemplifying embodiment applied to the dental field is provided by FIG. 2. In this example the sub-assembly (A) has been integrated into one single unit having the shape of a tool known under the name of dentist mirror.

The emitters with semi-conductors (3) are arranged all about the mirror (2a) proper. The latter reflects or sends the image of the subject back towards the light sensor (5) located at the end of the holding grip or handle (10) through a lens (2b). The holding grip or handle contains the electronic shaping means (6) and a connector (13) adapted to receive a signal transmission cable or wire.

The user has available a push button (11) adapted to activate the image freezing function.

The whole of the means of the sub-assembly (A) is therefore in this example given by way of illustration only which is not at all limiting, integrated into one single implement or appliance. The latter could be made fluid-tight and be sterilized in the same manner as the conventional dentist mirror.

FIG. 6 diagrammatically shows another examplary embodiment of a device for the acquisition of in particular colour images according to the invention. On this FIGURE the reference numeral 20 designates a member which comprises a for example cylindrical shell 21 which encloses in sealing relationship the active or operative parts of the image acquisition device such as the LED diodes 3, the C.C.D. type sensor 5, the electronic control device 6 to 10, these parts being arranged onto an integrated circuit plate 26. The shell or casing 21 comprises a window 28 for the emission and reception of the light of illumination and of the image of the object to be represented, this window comprising the aforesaid optical appliance. One end designated at 29 is designed as a sleeve or handle. The connection could be carried out by screw threading.

The shell or casing 21 is made from a material withstanding the thermal stresses thereby allowing after its separation from the sleeve 30 and after each use a sterilization of the member 20 within an autoclave for example at a temperature of 120° for one hour. In view of the provision of the LED diodes as light sources and of a C.C.D. type sensor, the member 20 may have a very small size for example with a diameter of 5 millimeters and a length of 15 millimeters.

FIG. 7 shows an advantageous embodiment of the image acquisition device which allows the removal of the influence of the ambient light which is harmful to the quality of the reproduced image. The device according to FIG. 7 comprises three elementary light emitting sources 3a to 3c. The sensor 5 is adapted to successively take four images, one image for each colour and one image taken in the ambient light. The colour images are separately stored in memories 7a to 7c and the image taken in the ambient light is stored in a memory 7s. A bipolar switch 32 with 4 positions a1 to c1 and s and a2 to c2 and s2 is provided for connecting the sensor 5 to the various memories for the storage of the individual images in synchronism with the activation of the elementary light sources. With each memory 7a to 7c is associated a device 33a to 33c the function of which is to substract during the establishment of the image resulting from three elementary monochromic images stored in the memories 7a to 7c, an image of the object taken in the ambient light and stored in the memory 7s to remove the influence of the ambient light.

From the description of the invention just made it appears that the image acquisition device according to the invention exhibits many advantages deriving in particular from the use of electroluminescent or laser diodes as light sources in combination with a light sensing device of the monochromic and charge coupled device type. Thus the image acquisition device according to the invention allows the emission of infrared rays rejecting filters and provides an embodiment of a small-sized device. The use of light emitters with semi-conductors provide a stable and calibrated light which makes it possible to proceed with accurate calorimetric analyses by making use of the device for instance for diagnosis purposes and for the taking of a tint during the manufacture of a dental prosthesis.

What is claimed is:

1. An endoscope for acquiring an image of an object and having a part insertable into a body cavity, comprising light source means for successively emitting monochromatic light in a plurality of colors different from one another, the monochromatic light being directed to the object to produce different color monochromatic images of the object, said light source means comprising at least one semi-conductor light emitting element which is overmodulatable in a pulse operating mode to emit each different color monochromatic light, each of said semi-conductor light emitting elements comprising an electroluminescent diode having a light emission power different for each color and a light emission cycle having a diode activation period and a diode non-activation period, light sensor means for sensing the different color monochromatic images, said light sensor means comprising a monochromatic charge coupled device and having a color sensitivity different for each color, signal processing means for receiving signals representative of the different color monochromatic images from said light sensor means and producing a color image of the object from said signals by sequential analysis, and means for compensating for differences between the light emission power of said diodes for the different color monochromatic images and for differences between the color sensitivity of said charge coupled device by varying the cyclic ratio of the diode activation period and the diode non-activation period during said light emission cycle of said diodes, the cyclic ratio being selected to enable an overmodulation of said diodes.

2. An endoscope for acquiring an image of an object, comprising light source means for successively emitting monochromatic light in a plurality of colors different from one another, the monochromatic light being directed to the object to produce different color monochromatic images of the object, said light source means comprising at least one semiconductor light emitting element which is overmodulatable in a pulse operating mode to emit each different color monochromatic light, each of said semi-conductor light emitting elements comprising an electroluminescent diode having a light emission power different for each color and a light emission cycle having a diode activation period and a diode non-activation period, said semi-conductor light emitting elements being arranged on a single substrate, said light source means further comprising a single optical device for the light emitted from said semi-conductor light emitting elements which is common to all of said semi-conductor light emitting elements, light sensor means for sensing the different color monochromatic images, said light sensor comprising a monochromatic charge coupled device and having a color sensitivity different for each color, signal processing means for receiving signals representative of the different color monochromatic images from said light sensor means and producing a color image of the object from said signals by sequential analysis, and means for compensating for differences between the light emission power of said diodes for the different color monochromatic images and for differences between the color sensitivity of said charge coupled device by varying the cyclic ratio of the diode activation period and the diode non-activation period during said light emission cycle of said diodes, the cyclic ratio being selected to enable an overmodulation of said diodes.

3. The endoscope of claim 2, wherein at least one of said semi-conductor light emitting elements comprises a plurality of said diodes to emit a single color of monochromatic light, the number of said diodes being selected to compensate for the differences in the light emission power and the color sensitivity of that single color.

4. The endoscope of claim 3, wherein said light source means and said light sensor means are arranged on a an integrated circuit plate.

5. The endoscope of claim 4, wherein said light emitting elements are arranged around said light sensor means on said integrated circuit plate.

6. The endoscope of claim 2, wherein said optical device comprises optical lenses or mirrors for modifying a radiation diagram of emitted light and adapting the object images to the size of said light sensor means.

7. The endoscope of claim 5, further comprising support means and a casing having a window, said casing retaining said light source means in a fluid-tight manner and being removably connectable in a fluid tight manner to said support means, said light emitting elements, said light sensor means and said signal processing means being arranged on a common substrate in front of said window such that light passes through said window.

8. The endoscope of claim 7, wherein said casing is made from a material capable of withstanding thermal stresses so as to constitute an assembly which can be sterilized after use and after separation from said support means in a sterilizing temperature condition.

9. In an endoscope for acquiring images of an object, having light emitting source means for illuminating the object and a light sensor of the monochromatic charge coupled device type for receiving the light representative of the image of the object, the improvement comprising at least one semi-conductor light emitter comprising a diode for each color of monochromatic light, said light emitters being arranged in said light emitting source means, said light emitting source means successively emitting monochromatic light of colors different from one another, signal processing means for receiving signals representative of the different color monochromatic images from the sensor and producing a color image of the object from said signals by sequential analysis, means for successively activating said diodes to emit light of different colors, means for obtaining an image of the object in ambient light, and means for subtracting the image of the object in ambient light from the monochromatic color images to remove the effect of the ambient light from the monochromatic color images.

10. The endoscope of claim 9, wherein said diode is an electroluminescent diode.

11. The endoscope of claim 9, wherein said diode is a laser diode.

12. An endoscope for acquiring an image of an object, comprising light source means for successively emitting monochromatic light in a plurality of colors different from one another, the monochromatic light being directed to the object to produce different color monochromatic images of the object, said light source means comprising at least one semi-conductor light emitting element for emitting each different color monochromatic light, each of said semi-conductor light emitting elements comprising an electroluminescent diode arranged to provide a light emission power different for each color, said semi-conductor light emitting elements being arranged on a single substrate, light sensor means for sensing the different color monochromatic images, said light sensor means comprising a monochromatic charge coupled device and having a color sensitivity different for each color, an optical device through which light is passed to said light sensor means, all of the different color monochromatic light being passed through said optical device, and signal processing means for receiving signals representative of the different color monochromatic images from said light sensor means and producing a color image of the object from said signals by sequential analysis, the number of said semi-conductor light emitting diodes being different for each different color monochromatic light such that light power differences and sensitivity differences between different color light is compensated for.

* * * * *